US012678295B2

(12) United States Patent
Fan et al.

(10) Patent No.: US 12,678,295 B2
(45) Date of Patent: Jul. 14, 2026

(54) 3D PRINTING SELF-STABILIZING CERVICAL INTERBODY FUSION CAGE

(71) Applicant: The Third Hospital of Changsha, Changsha City (CN)

(72) Inventors: Lei Fan, Changsha City (CN); Qing Lei, Changsha City (CN); Li Chen, Changsha City (CN); Minghui Jiang, Changsha City (CN)

(73) Assignee: The Third Hospital of Changsha, Chungsha City (CN)

( * ) Notice: Subject to any disclaimer, the term of this patent is extended or adjusted under 35 U.S.C. 154(b) by 0 days.

(21) Appl. No.: 18/913,054

(22) Filed: Oct. 11, 2024

(65) Prior Publication Data

US 2026/0102258 A1 Apr. 16, 2026

(51) Int. Cl.
*A61F 2/44* (2006.01)
*A61F 2/30* (2006.01)
*B33Y 80/00* (2015.01)

(52) U.S. Cl.
CPC .......... *A61F 2/447* (2013.01); *A61F 2/30749* (2013.01); *B33Y 80/00* (2014.12); *A61F 2002/30131* (2013.01); *A61F 2002/30154* (2013.01)

(58) Field of Classification Search
CPC ................. A61F 2/447; A61F 2/30749; A61F 2002/30131; A61F 2002/30154; A61F 2002/448; A61F 2/446; A61F 2/4465; A61F 2/4455; A61F 2/449
See application file for complete search history.

(56) References Cited

U.S. PATENT DOCUMENTS

| | | | | |
|---|---|---|---|---|
| 10,299,938 B1 * | 5/2019 | Ehteshami | .............. | A61F 2/447 |
| 11,123,201 B2 * | 9/2021 | Ehteshami | .......... | A61F 2/30749 |
| 11,351,038 B2 * | 6/2022 | Blain | .................... | A61F 2/4455 |
| 11,510,708 B2 * | 11/2022 | Lewis | .................. | A61B 17/846 |
| 2007/0043369 A1 * | 2/2007 | Wallenstein | ....... | A61B 17/8033 606/279 |
| 2008/0249575 A1 * | 10/2008 | Waugh | .................... | A61F 2/447 606/301 |
| 2011/0208311 A1 * | 8/2011 | Janowski | .............. | A61F 2/4425 623/17.16 |
| 2013/0060337 A1 * | 3/2013 | Petersheim | ............... | A61F 2/46 623/17.16 |
| 2020/0352739 A1 * | 11/2020 | Ouidja | ................ | A61F 2/30749 |

* cited by examiner

*Primary Examiner* — Eduardo C Robert
*Assistant Examiner* — Holly Joanna Lane
(74) *Attorney, Agent, or Firm* — WCF IP

(57) ABSTRACT

A novel 3D (three-dimensional) printing self-stabilizing cervical interbody fusion cage is provided, including a fusion cage body, circular-arc notches arranged at four corners of a front side surface of the fusion cage body, and threaded openings are formed in interiors of the circular arc notches and screws are correspondingly mounted in the threaded openings. An inner wall of the fusion cage body is of a circular arc structure, and a reserved circular opening is formed in the middle position of the front side surface. Each of the circular arc notches is positioned to form an angle of 45° with a horizontal plane of each of the four corners of the fusion cage body. Screw are self-tapping screws with threads, and the threads of the screws are in fit with threads of the inner walls of the circular arc notches.

5 Claims, 4 Drawing Sheets

3D PRINTING SELF-STABILIZING CERVICAL INTERBODY FUSION CAGE

TECHNICAL FIELD

The present disclosure relates to the technical field of medical prostheses manufacturing, and in particular to a novel 3D (three-dimensional) printing self-stabilizing cervical interbody fusion cage.

BACKGROUND

With the change of human life and work style, the incidence of cervical spondylosis is increasing year by year, which has become a common and frequently-occurring disease endangering human health. The cervical spondylosis often causes dizziness, numbness of limbs, weakness, nausea, and other uncomfortable symptoms, and may lead to high paraplegia in severe cases, which brings heavy economic burden to society and families.

One of the classical surgical methods for the treatment of cervical spondylosis is anterior cervical corpectomy and bone graft fusion surgery, which is a common surgical method for the clinical treatment of multi-segmental cervical spondylosis in the past. After the cervical intervertebral disc and part of the vertebral body in the diseased segment are removed, the intervertebral disc and part of the vertebral body which are completely decompressed and taken out to form a disarticulated space, which is filled by an intervertebral fusion cage, thus connects the upper adjacent vertebral body and the lower adjacent vertebral body. The filling material may be autogenous iliac bone, or allogeneic bone, artificial bone grafting material, etc. These materials are packed in the cage to induce bone healing and growth, which has the advantages of improving the fusion rate of bone grafting, maintaining and restoring intervertebral space height, etc. Another method is to use a titanium cage and other things similar to bone blocks instead of bones to be placed in the disarticulated space, which can achieve the same effect as the iliac bone. After the bone grafting is completed, in order to ensure the stability of bone grafting, it is required to use a titanium plate screw internal fixation system on the surface of cervical vertebra to maintain the position of grafted bone block and the height of vertebral body, and improve the fusion rate.

The immediate stability and long-term fusion rate of the postoperative cervical spine are the key to the success of operation, and have always been the focus of attention in the field of orthopedics. However, the existing self-stabilizing cervical interbody fusion cage is difficult to meet the immediate stability and long-term fusion rate of the postoperative cervical spine at the same time. Therefore, it is necessary to provide a novel 3D printing self-stabilizing cervical interbody fusion cage to solve the above technical problems.

SUMMARY

A novel 3D printing self-stabilizing cervical interbody fusion cage is provided in the present disclosure, which solves the problems that the existing self-stabilizing cervical interbody fusion cage is difficult to meet the requirement of anterior cervical corpectomy and bone graft fusion surgery and difficult to simultaneously meet the requirement of the interbody fusion cage products with a titanium cage and the other instead of bones for placement.

In order to solve the technical problem above, a novel 3D printing self-stabilizing cervical interbody fusion cage is provided, including a fusion cage body and circular arc notches.

The circular arc notches are arranged at four corners of a front side surface of the fusion cage body, and threaded openings are formed in interiors of the circular arc notches, and screws are correspondingly mounted in the threaded openings;

An inner wall of the fusion cage body is of a circular arc structure, a reserved circular opening is formed in a middle position of the front side surface, and a square opening is formed in a side surface of the fusion cage body.

The fusion cage body and the screws are integrally formed by 3D printing, and are made of carbon fiber reinforced PEE (polyether ester) materials. The square opening and the reserved circular opening are arranged convenient for bone grafting.

Preferably, each of the circular arc notches is positioned to form an angle of 45° with a horizontal plane of each of four corners of the fusion cage body.

Preferably, the screws are self-tapping screws with threads, and the threads of the screws are in fit with threads of inner walls of the circular arc notches.

Preferably, first concave-convex groove plates are mounted at upper and lower positions of the front side surface of the fusion cage body.

Preferably, square grooves are mounted on both sides of the reserved circular opening, and multiple triangular grooves are mounted at upper and lower positions of a back surface of the fusion cage body.

Both the square grooves and the triangular grooves are concave-convex grooves, which are convenient for positioning and fixing.

Preferably, second concave-convex groove plates are mounted at an outer side of the back surface of the fusion cage body.

The second concave-convex groove plates and the first concave-convex groove plates have a same structure, i.e., a concave-convex groove structure on the surface to facilitate the fixation.

Preferably, a diameter of each of the screws is 2.5 mm, and a length of each of the screw is capable of being selected as required.

Compared with the related technology, a novel 3D printing self-stabilizing cervical interbody fusion cage provided by the present disclosure has the following beneficial effects that:

The novel 3D printing self-stabilizing cervical interbody fusion cage provided by the present disclosure can meet immediate stability of the postoperative cervical vertebra and improve the long-term fusion rate, can conform to the concept of zero profile and reduce the complications of the posterior pharyngeal wall after operation, thus improving the success rate of operation. A titanium plate screw for reinforcement and maintenance is avoid to use, the operation steps are simplified, hemorrhage during operation is reduced, and patient cost is lowered.

REFERENCE NUMBERS IN THE DRAWINGS

1—fusion cage body; 2—circular arc notch; 3—screw; 4—first concave-convex groove plate; 5—reserved circular opening; 6—square groove; 7—square opening; 8—triangular groove; 9—second concave-convex groove plate; 10—extended circular opening.

DETAILED DESCRIPTION OF THE EMBODIMENTS

The present disclosure is further described below with reference to accompanying drawings and specific embodiments.

First Embodiment

Figure 1:
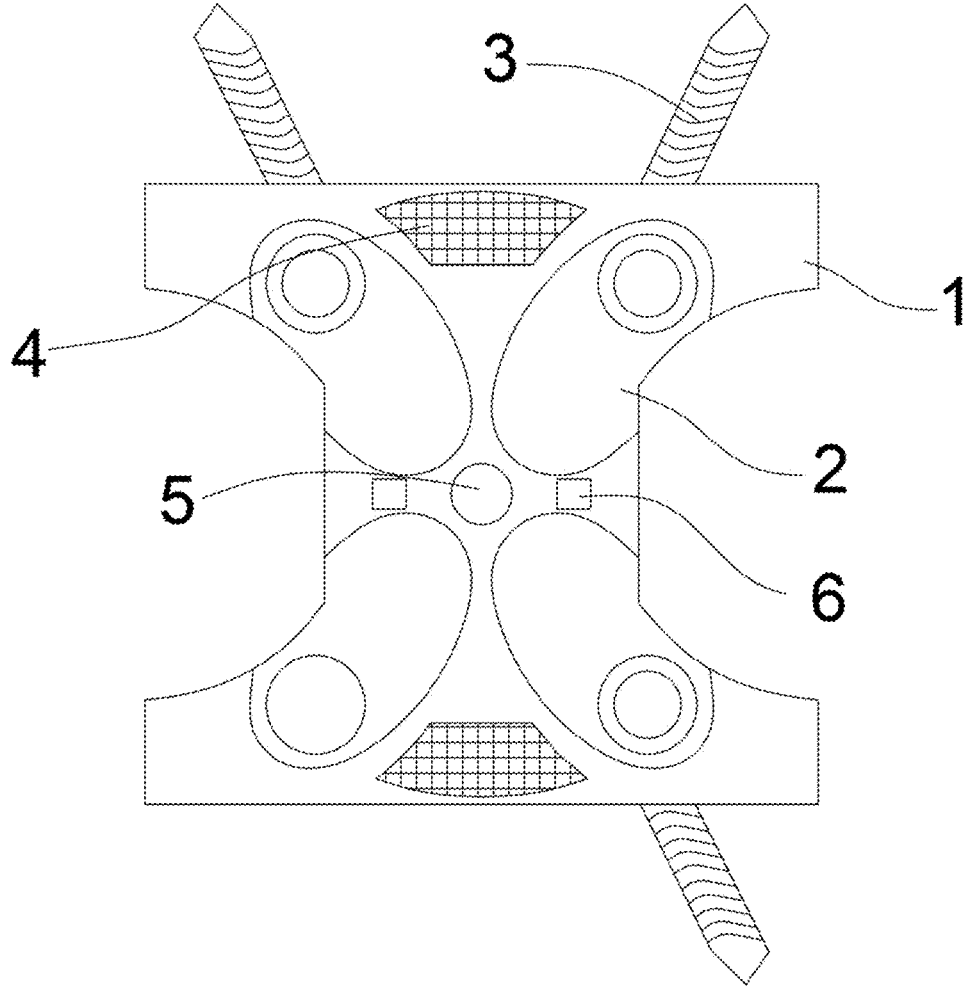
FIG. 1 is a structural diagram of a first embodiment of a novel 3D printing self-stabilizing cervical interbody fusion cage according to the present disclosure.
Figure 2:
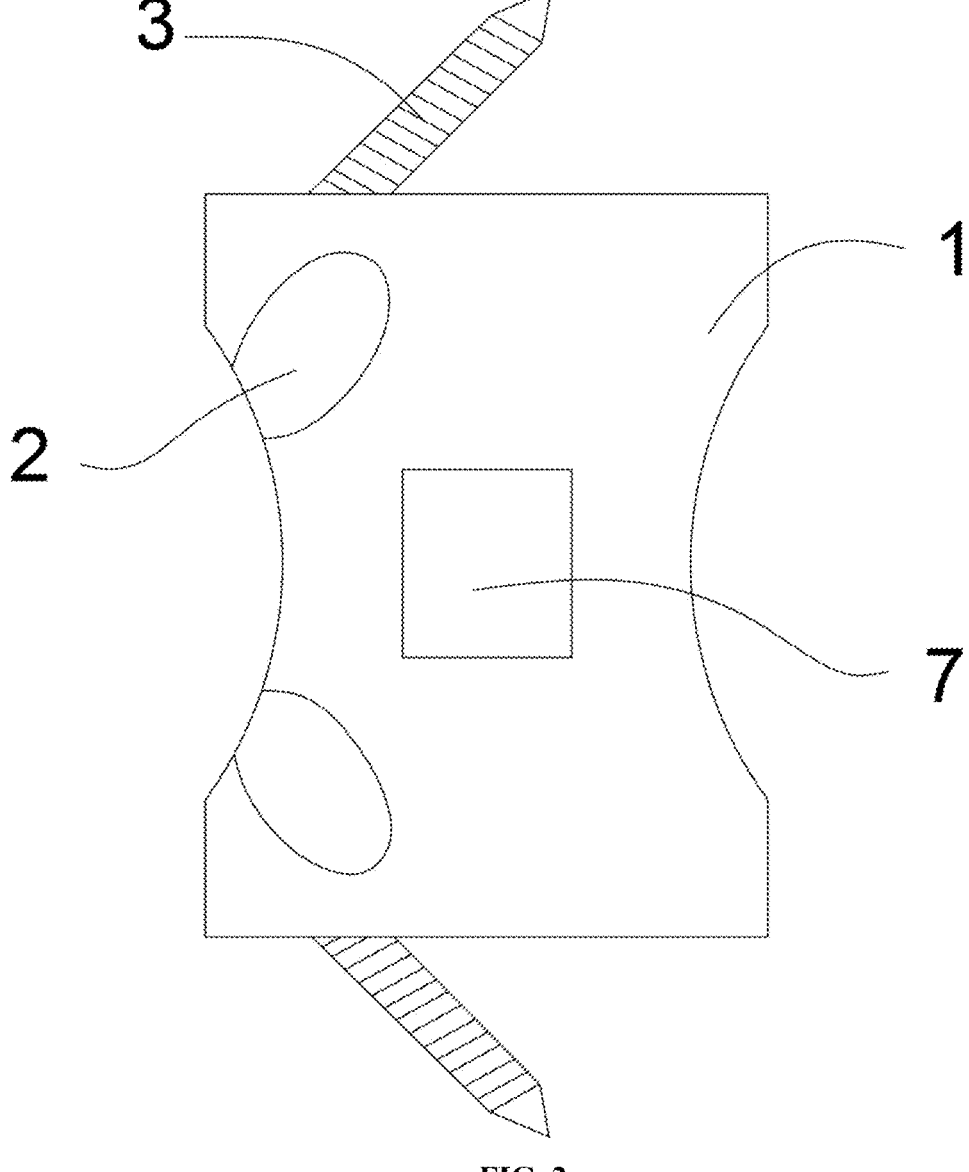
FIG. 2 is a side view of a novel 3D printing self-stabilizing cervical interbody fusion cage according to the present disclosure.
Figure 3:
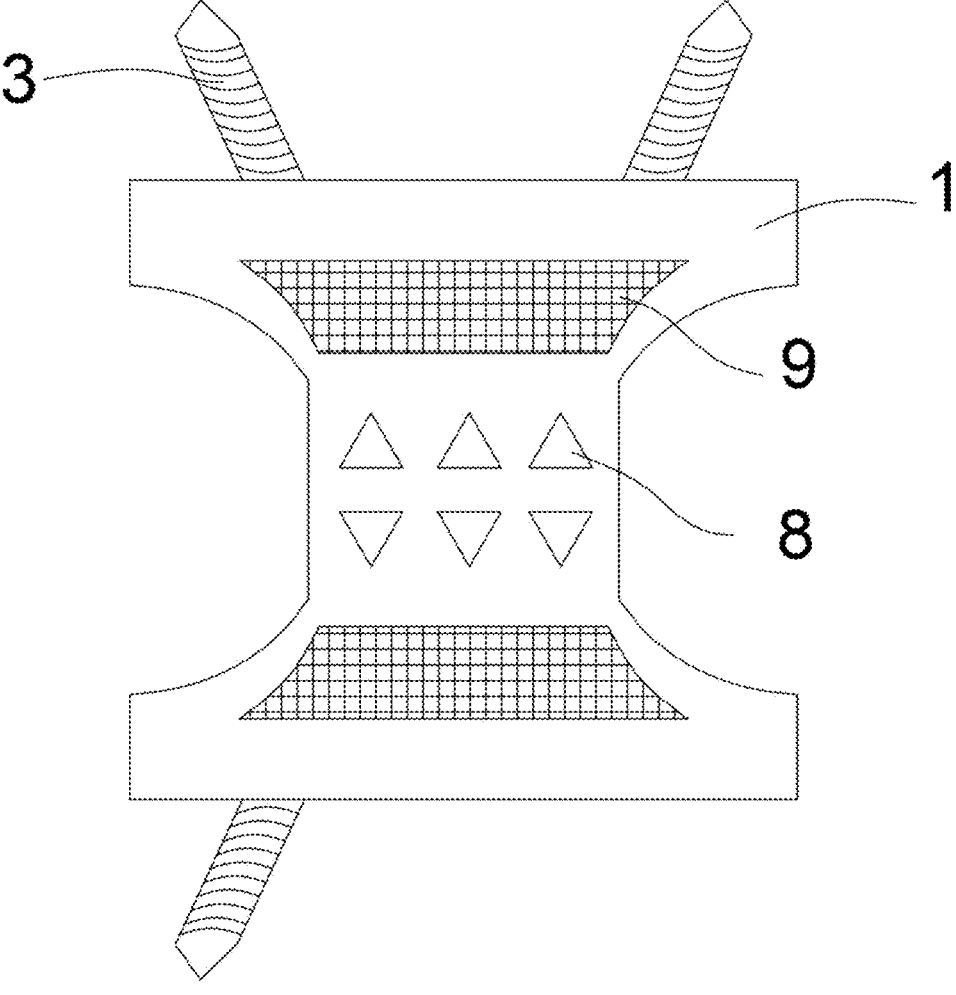
FIG. 3 is a structural diagram of a back surface of a novel 3D printing self-stabilizing cervical interbody fusion cage according to the present disclosure.

Referring to FIG. 1, FIG. 2, and FIG. 3, FIG. 1 is a structural diagram of a first embodiment of a novel 3D printing self-stabilizing cervical interbody fusion cage according to the present disclosure. FIG. 2 is a side view of a novel 3D printing self-stabilizing cervical interbody fusion cage according to the present disclosure. FIG. 3 is a structural diagram of a back surface of a novel 3D printing self-stabilizing cervical interbody fusion cage according to the present disclosure. A novel 3D printing self-stabilizing cervical interbody fusion cage includes a fusion cage body 1 and circular arc notches 2. The circular arc notches 2 are arranged at four corners of a front side surface of the fusion cage body 1, and threaded openings are formed in interiors of the circular arc notches 2, and screws 3 are correspondingly mounted in the threaded openings.

An inner wall of the fusion cage body 1 is of a circular arc structure, a reserved circular opening 5 is formed in the middle position of the front side surface, and a square opening 7 is formed in a side surface of the fusion cage body 1.

Both the fusion cage body 1 and the screws 3 are integrally formed by 3D printing, and are made of carbon fiber reinforced PEE materials. The square opening 7 and the reserved circular opening 5 are arranged convenient for bone grafting.

Each of the circular arc notches 2 is positioned to form an angle of 45° with a horizontal plane of each of four corners of the fusion cage body 1.

The screws 3 are self-tapping screws with threads, and the threads of the screws 3 are in fit with threads of inner walls of the circular arc notches 2.

First concave-convex groove plates 4 are mounted at upper and lower positions of the front side surface of the fusion cage body 1.

Square grooves 6 are mounted on both sides of the reserved circular opening 5, and multiple triangular grooves 8 are mounted at upper and lower positions of a back surface of the fusion cage body 1.

Both the square grooves 6 and the triangular grooves 8 are concave-convex grooves, which are convenient for positioning and fixing.

Second concave-convex groove plates 9 are mounted at an outer side of the back surface of the fusion cage body 1.

The second concave-convex groove plates 9 and the first concave-convex groove plates 4 have a same structure, i.e., a concave-convex groove structure on the surface, to facilitate the fixation.

A diameter of each of the screws 3 may be 2.5 mm, and a length of each of the screws can be selected as required.

The working principle of the novel 3D printing self-stabilizing cervical interbody fusion cage provided by the present disclosure is as follows: when in use, after a patient is generally anesthetized, the patient is placed in a supine position, neck hyperextension position, the patient head is deviated to the left; after conventional draping and disinfection, a longitudinal incision is made in anterior right side of the neck of the patient to cut the skin, subcutaneous and platysma muscle layer by layer; prevertebral space is accessed along an approach between the vascular sheath and visceral sheath, and omohyoid muscle is cut off in the approach; and under the perspective of a C-buttock machine, diseased intervertebral space is determined definitely, the adjacent vertebral bodies are fixed, the diseased segmental vertebral bodies are completely resected, thus completely decompressing; autogenous bone and artificial bone are filled and compacted into a 3D printed fusion cage body 1 and screws 3, which are integrally placed into a bone graft bed, and four screws 3 are screwed into the upper and lower adjacent vertebral bodies for fixing; and after the implant is observed to reach an ideal position under the perspective of the C-buttock machine, washing is made with saline, bleeding is stopped, and the incision is sutured layer by layer.

Compared with the related art, a novel 3D printing self-stabilizing cervical interbody fusion cage provided by the present disclosure has the following beneficial effects that:

The novel 3D printing self-stabilizing cervical interbody fusion cage can meet immediate stability of the postoperative cervical vertebra and improve the long-term fusion rate, can conform to the concept of zero profile and reduce the complications of the posterior pharyngeal wall after operation, thus improving the success rate of operation. A titanium plate screw for reinforcement and maintenance is avoided to use, the operation steps are simplified, hemorrhage during operation is reduced, and patient cost is lowered.

Second Embodiment

Figure 4:
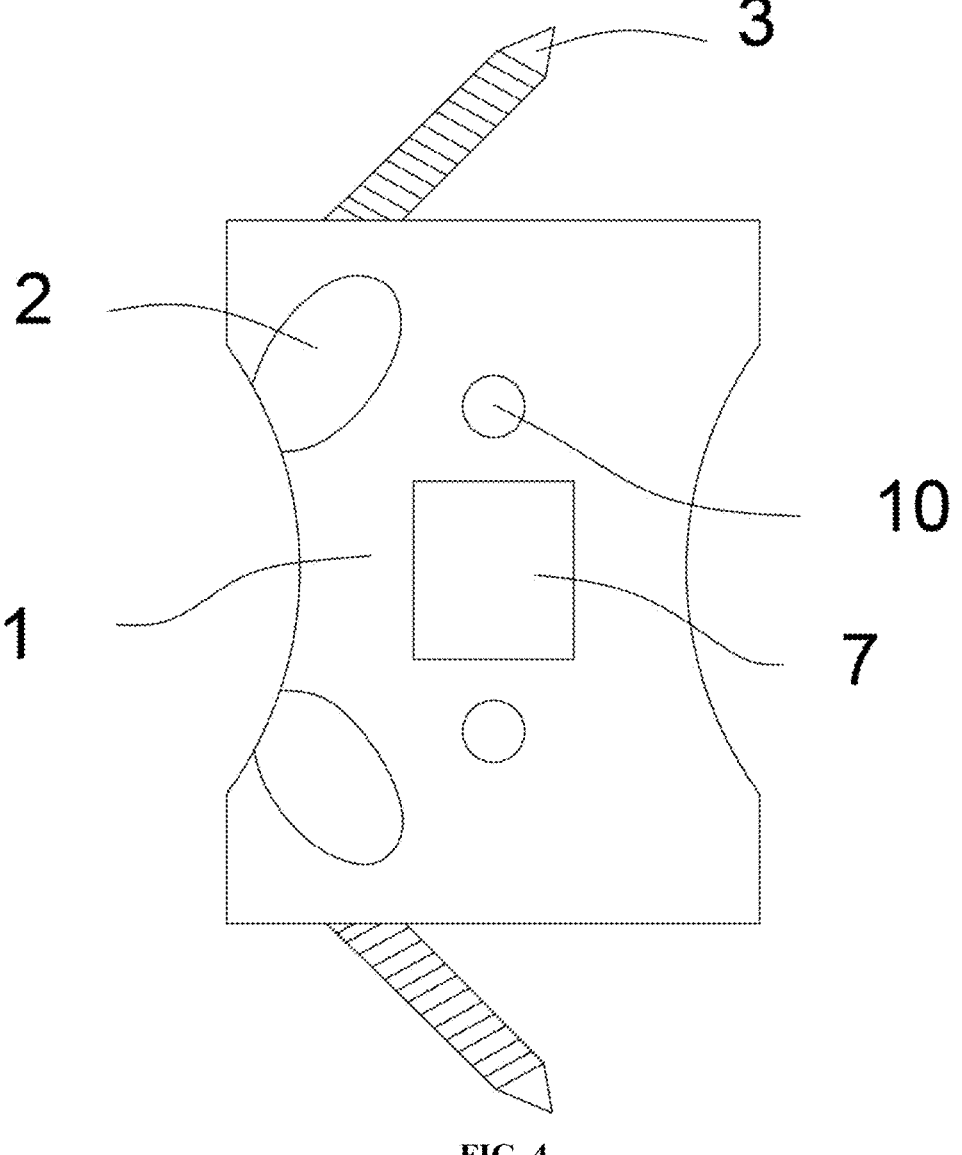
FIG. 4 is a structural diagram of a second embodiment of a novel 3D printing self-stabilizing cervical interbody fusion cage according to the present disclosure.

Referring to FIG. 4, FIG. 4 is a structural diagram of a second embodiment of a novel 3D printing self-stabilizing cervical interbody fusion cage according to the present disclosure. Based on a novel 3D printing self-stabilizing cervical interbody fusion cage provided by the first embodiment of the present disclosure, the second embodiment of the present disclosure provides another novel 3D printing self-stabilizing cervical interbody fusion cage. The second embodiment is only a preferred embodiment of the first embodiment, and the implementation of second embodiment will not affect the independent implementation of the first embodiment.

Specifically, the difference of the novel 3D printing self-stabilizing cervical interbody fusion cage provided by the second embodiment of the present disclosure is that the novel 3D printing self-stabilizing cervical interbody fusion cage is provided with extended circular openings 10 formed at upper and lower ends of the surface of the fusion cage body 1.

The working principle is that in the working process, the extended circular openings 10 can further facilitate the bone grafting.

The beneficial effects are that the extended circular openings 10 can further facilitate the bone grafting.

The above is only the embodiment of the present disclosure, and is not intended to limit the patent scope of the present disclosure. Any equivalent structure or equivalent process transformation made by using the contents of the specification and drawings of the present disclosure, or direct or indirect application to other related technical fields, are equally included in the scope of patent protection of the present disclosure.

What is claimed is:

1. A three dimensional (3D) printed self-stabilizing interbody fusion cage, comprising:
  a fusion cage body, comprising
    a front side surface with four corners, wherein first concave-convex groove plates are mounted at upper and lower positions of the front side surface of the fusion cage body,
    wherein circular arc notches are formed in each of the four corners, and wherein interiors of each of the circular arc notches comprise threaded openings, and
    wherein a reserved circular opening formed in a middle portion of the front side surface of the fusion cage body, wherein the fusion cage body comprises an inner wall of a circular arc structure, and
  a side surface, wherein said side surface comprises a square opening; and screws mounted in the threaded openings of the fusion cage body, wherein the screws are self-tapping screws with threads, and the threads of the screws are in fit with threads of inner walls of the circular arc notches, wherein the fusion cage body and the screws are integrally formed by 3D printing.

2. The novel 3D printing self-stabilizing cervical interbody fusion cage according to claim 1, wherein each of the circular arc notches is positioned to form an angle of 45° with a horizontal plane of each of four corners of the fusion cage body.

3. The novel 3D printing self-stabilizing cervical interbody fusion cage according to claim 1, wherein square grooves are mounted on both sides of the reserved circular opening, and a plurality of triangular grooves are mounted at upper and lower positions of a back surface of the fusion cage body.

4. The novel 3D printing self-stabilizing cervical interbody fusion cage according to claim 1, wherein second concave-convex groove plates are mounted at an outer side of a back surface of the fusion cage body.

5. The novel 3D printing self-stabilizing cervical interbody fusion cage according to claim 1, wherein a diameter of each of the screws is 2.5 mm, and a length of each of the screws is capable of being selected as required.

* * * * *